(12) United States Patent
Marlinski

(10) Patent No.: US 10,779,764 B2
(45) Date of Patent: Sep. 22, 2020

(54) SYSTEMS AND METHODS FOR PROPRIOCEPTIVE STIMULATION TO PREVENT UNINTENTIONAL FALLS

(71) Applicant: DIGNITY HEALTH, San Francisco, CA (US)

(72) Inventor: Vladimir Marlinski, Phoenix, AZ (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 16/469,496

(22) PCT Filed: Dec. 20, 2017

(86) PCT No.: PCT/US2017/067545
§ 371 (c)(1),
(2) Date: Jun. 13, 2019

(87) PCT Pub. No.: WO2018/119047
PCT Pub. Date: Jun. 28, 2018

(65) Prior Publication Data
US 2019/0350517 A1    Nov. 21, 2019

Related U.S. Application Data

(60) Provisional application No. 62/436,559, filed on Dec. 20, 2016.

(51) Int. Cl.
*A61B 5/0482* (2006.01)
*A61B 5/00* (2006.01)
(Continued)

(52) U.S. Cl.
CPC ............ *A61B 5/486* (2013.01); *A61B 5/1117* (2013.01); *A61B 5/1123* (2013.01);
(Continued)

(58) Field of Classification Search
CPC ..... A61B 5/486; A61B 5/1117; A61B 5/1123; A61B 5/6823; A61B 5/6828; A61B 5/7455; A61B 2562/0219; G09B 19/00
(Continued)

(56) References Cited

U.S. PATENT DOCUMENTS

2006/0052834 A1   3/2006   Goroszeniuk
2009/0221943 A1   9/2009   Burbank et al.
(Continued)

FOREIGN PATENT DOCUMENTS

WO    2008088985    7/2008

OTHER PUBLICATIONS

International Search Report and Written Opinion, International Application No. PCT/US2017/067545, dated Mar. 2018.

*Primary Examiner* — Robert P Bullington

(57) ABSTRACT

Systems, devices, and methods are provided for reducing a risk of unintentional falls in a subject that is at risk for falls. The device includes a sensor and a stimulator. The sensor is configured to be positioned adjacent a body portion of the user that changes orientation when the user sits and stands. The sensor is also configured to emit an activation signal when the user stands and to emit a deactivation signal when the user sits or lies down. The stimulator is in communication with the sensor and is configured to be positioned adjacent one of a calf and a lower back of the user. The stimulator is configured to vibrate at a frequency that stimulates proprioceptors of the user without inducing muscle contractions upon receipt of the activation signal from the sensor and to cease vibration upon receipt of the deactivation signal from the sensor.

13 Claims, 6 Drawing Sheets

(51) Int. Cl.
*A61B 5/11* (2006.01)
*G09B 19/00* (2006.01)

(52) U.S. Cl.
CPC .......... *A61B 5/6823* (2013.01); *A61B 5/6828* (2013.01); *A61B 5/7455* (2013.01); *G09B 19/00* (2013.01); *A61B 2562/0219* (2013.01)

(58) Field of Classification Search
USPC ........................................................ 434/258
See application file for complete search history.

(56) References Cited

U.S. PATENT DOCUMENTS

| | | |
|---|---|---|
| 2014/0163444 A1 | 6/2014 | Ingvarsson et al. |
| 2014/0179986 A1 | 6/2014 | Kelley |
| 2014/0249601 A1 | 9/2014 | Bachinski et al. |
| 2016/0331963 A1 | 11/2016 | George |
| 2016/0354603 A1 | 12/2016 | Keenan et al. |

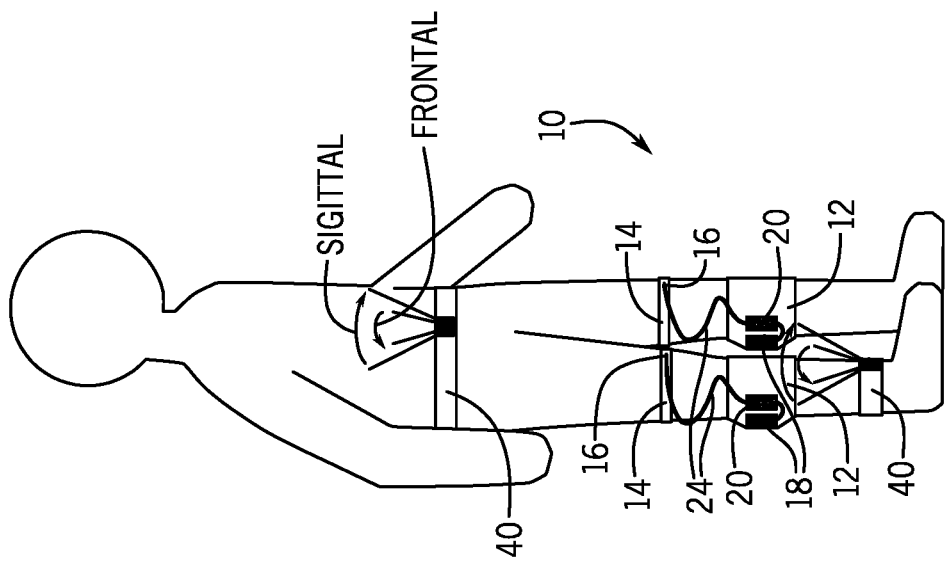
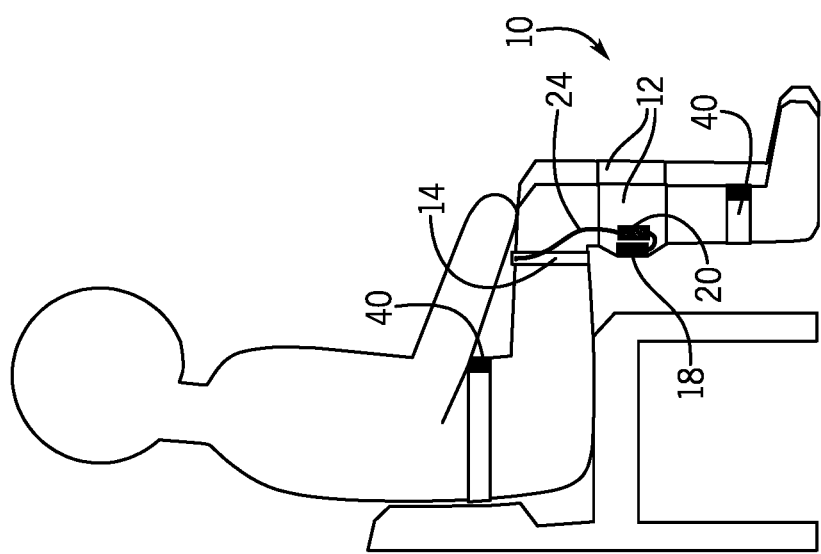

SYSTEMS AND METHODS FOR PROPRIOCEPTIVE STIMULATION TO PREVENT UNINTENTIONAL FALLS

CROSS-REFERENCE TO RELATED APPLICATIONS

This application represents the U.S. National Stage of International Application No. PCT/US2017/067545 filed Dec. 20, 2017 which claims the benefit of U.S. Provisional Patent Application No. 62/436,559 filed on Dec. 20, 2016, the entire contents of which are incorporated herein by reference.

FIELD

Embodiments of the present disclosure are generally directed to systems, methods, and devices for proprioceptive stimulation to prevent and/or reduce the risk of unintentional falls, for example, in subjects at an increased risk of falls.

BACKGROUND

Aging is related to reductions in physical function, contributing to inactivity, frailty, and incident falls. More specifically, senior persons generally experience a decline in their ability to flawlessly execute a complex skill for body equilibrium during standing and walking. This skill of maintaining equilibrium, which is learned and perfected through the first several years of human life, is based on fine tuning the activity of numerous components of the neuromuscular system. With increasing age, the efficiency of these components declines and, in turn, system function deteriorates. Muscles lose their mass, strength, and power, which is known as sarcopenia and dynopenia. Proprioceptors, muscle spindles, and tendon organs, which detect muscle length and force, degenerate and their numbers reduce. The amount of neural fibers innervating muscles declines, and the velocity of signal transmissions via surviving neural fibers reduces due to demyelinization. Additionally, with respect to the brain, the gray matter of the cerebral cortex, the thalamus, and the cerebellum shrinks and reduces in volume at a rate of about 5 cm^3 per year, while the volume of white matter, consisting of neuronal fibers connecting different parts of the brain and spinal cord, also becomes smaller.

The first manifestation of age-related deterioration of body equilibrium is an increase in body sway during standing. As an increased magnitude of body movement can increase posture instability, elders can eventually lose their balance and fall, suffering bone fractures, joint dislocations, concussions, and even death. For example, every year, an estimated 30-40% of elders over the age of 65 may fall at least once, and such falls lead to injuries, loss of independence, or death in about 33% of those who fall. Given the serious impact of falls on the elderly population, there is a need for devices and methods to improve balance and decrease fall risk.

SUMMARY

Embodiments of the present disclosure provide systems, devices, and methods for reducing a risk of unintentional falls in a subject at risk for falls. For example, some embodiments include a device comprising at least one stimulator supported by a first support member and at least one sensor supported by a second support member. The device can be configured and arranged so that the at least one sensor is in operative communication with the at least one stimulator. Moreover, the at least one sensor can activate the stimulator when a user is in a substantially standing position and deactivate the stimulator when the user in a substantially seated position. In some embodiments, the stimulator can be configured to stimulate proprioceptors of the user at a frequency that does not induce muscle contractions.

In one aspect, a device for providing proprioceptive stimulation to a user is provided. The device includes a first support member, a second support member, a stimulator, and a sensor. The first support member and the second support member are each configured to be worn by the user. The stimulator is at least partially supported by the first support member and is configured to stimulate proprioceptors of the user at a vibration frequency that does not induce muscle contraction. The sensor is at least partially supported by the second support member and is configured to control operation of the stimulator based on an orientation of the user.

In another aspect, a method of reducing a risk of unintentional falls in a user is provided. The method includes a device configured to be worn by the user, including a stimulator configured to be positioned adjacent a body portion of the user and a sensor configured to be positioned adjacent to an upper leg of the user. The sensor is in communication with the stimulator and is configured to provide an activation signal when the user is in a substantially standing position. The method also includes donning the device by the user, and activating the stimulator via the activation signal from the sensor when the user is in the substantially standing position. Activating the stimulator according to the present method causes the stimulator to vibrate against the body portion of the user at a frequency that stimulates proprioceptors of the user.

In yet another aspect, a device for providing proprioceptive stimulation to a user is provided. The device includes a sensor and a stimulator. The sensor is configured to be positioned adjacent a body portion of the user that changes orientation when the user sits and stands. The sensor is also configured to emit an activation signal when the user stands and to emit a deactivation signal when the user sits or lies down. The stimulator is in communication with the sensor and is configured to be positioned adjacent one of a calf and a lower back of the user. The stimulator is configured to vibrate at a frequency that stimulates proprioceptors of the user without inducing muscle contractions upon receipt of the activation signal from the sensor and to cease vibration upon receipt of the deactivation signal from the sensor.

Additional objectives, advantages and novel features will be set forth in the description which follows or will become apparent to those skilled in the art upon examination of the drawings and detailed description which follows.

BRIEF DESCRIPTION OF THE DRAWINGS

FIGS. 2A and 2B are schematic illustrations of the device of FIG. 1 donned by a user, where FIG. 2A depicts the user wearing the device while in a seated position and FIG. 2B depicts the user wearing the device while in a standing position.

FIG. 4A illustrates changes in Center of Mass (COM) range during standing with 30 Hz proprioceptive stimulation as a function of COM range during standing without proprioceptive stimulation in young subjects, and FIG. 4B illustrates changes in COM range during standing with 30 Hz proprioceptive stimulation as a function of COM range during standing without proprioceptive stimulation in elderly subjects.

FIGS. 5A, 5B, and 5C are bar graphs illustrating average COM sway without and with proprioceptive vibration for the HY group, the HE group, and the FR group, respectively, and FIGS. 5D, 5E, and 5F are graphs illustrating COM sway during proprioceptive vibration as a function of baseline (i.e., no vibration) COM sway for the HY group, the HE group, and the FR group, respectively.

Corresponding reference characters indicate corresponding elements among the view of the drawings. The headings used in the figures should not be interpreted to limit the scope of the claims.

DETAILED DESCRIPTION

Figure 1:
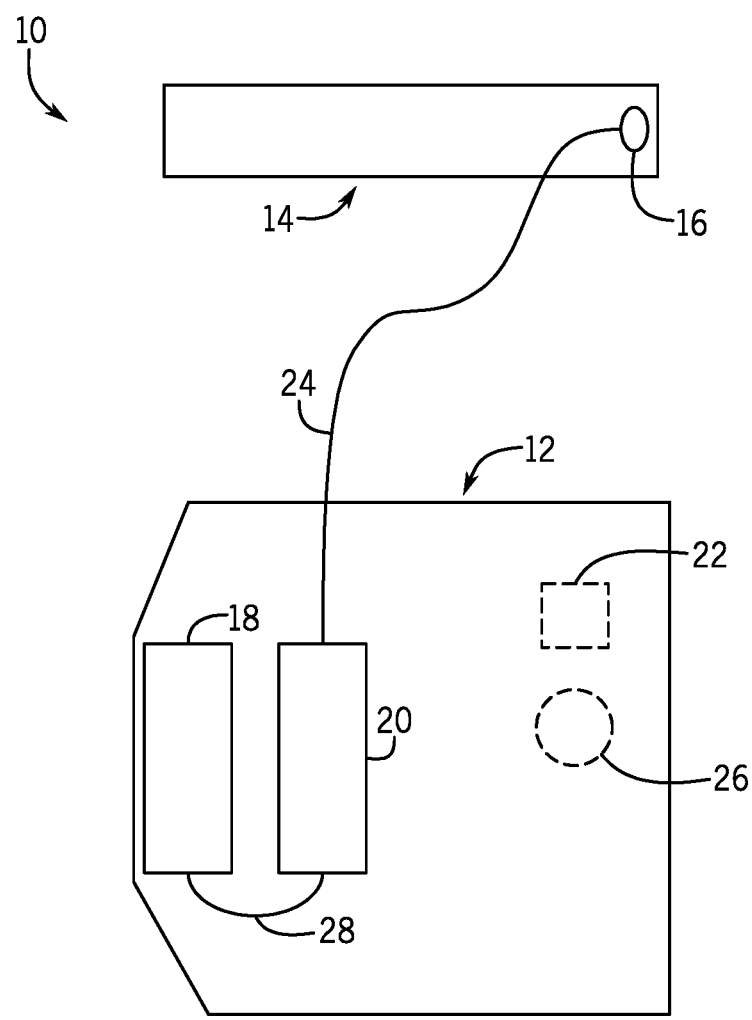
FIG. 1 is a schematic illustration of a device according to some embodiments.

Given the serious impact of falls on the elderly population, there is a need for strategies to improve balance and decrease fall risk. A potentially efficient strategy may be developed based on enhancing weak signals via background near-threshold noise in sensory and motor systems, known as stochastic resonance. Prior work has shown that low-level stochastic stimulation elicited by vibration of soles of the feet and electrical pulses applied to the knee can enhance the postural performance of elderly people. The present disclosure provides systems and methods that translate these finding into real-world solutions to aid in reducing the risk of unintentional falls.

More specifically, some embodiments provide a device and methods for delivering proprioceptive stimulation to an individual, user, subject, or patient (hereinafter, termed "user"). The device can be configured to reduce the risk of and/or prevent unintentional losses of balance for users in need thereof. For example, the device can be employed by any user (e.g., regardless of age, gender, sex, etc.) that suffers from reduced balance and/or experiences an increased likelihood of suffering from an unintentional fall or loss of balance.

Accordingly, some embodiments can improve a user's balance by stimulating one or more biological tissues to enhance balance and/or to substantially reduce or prevent the risk of unintentional falls. Without being necessarily bound by any theory, some embodiments of the device and methods herein are based on the following information and principles.

Generally, the magnitude of body sway in a user depends on detection and processing of signals in somatosensory, visual, and vestibular systems involved in maintenance of balance. A first postural response for maintaining balance in a user can be a motor activity known as the ankle strategy, which foremost involves activation of muscles crossing the ankle joint, such as the gastrocnemius and the tibialis anterior. For example, while in a substantially vertical position (e.g., standing), small angular deviations occur in the ankle joint. These deviations can result in a change in length of attached muscles, which can be detected by proprioceptors (i.e., muscle spindles). Signals from proprioceptors can then be directed to motor neurons, which activate the parent muscles to restore joint position (that is, to counteract the deviations). Noteworthy, postural responses are not limited to activation of the ankle muscles but can involve activation of other anti-gravitational muscles crossing the knee and the hip, such as the quadriceps muscle group, the biceps femoris, and any other muscle of the leg, as well as abdominal and spine muscles.

As a user ages, the efficiency of this response loop declines. More specifically, with age, the sensitivity of sensory systems degrades and motor neurons become less responsive to changes in sensory signals. The subject's neuromuscular system is, thus, more apt to making mistakes (e.g., by not sensing deviations or not correctly responding to sensed deviations in posture), which can cause loss of balance and/or unintentional falls.

It is suggested that the deterioration of signal processing in sensory and motor systems, to some extent, can be compensated by applying auxiliary random low-intensity stimulation, which produces the effect of stochastic resonance. Indeed, an application of such stochastic resonance to a division of the somatosensory system responsible for cutaneous sensation has been shown to enhance postural stability during both standing and walking. Sole vibrations with random frequencies and magnitude (below a threshold for producing perception) for activating plantar mechanoreceptors have been shown to improve balance and gait in healthy elderly people. Also, an increased body sway in patients with diabetic neuropathy and stroke was reduced using subsensory mechanical noise applied to soles of feet. Stimulation with a low-level electrical noise applied at the knee, which presumably activated cutaneous receptors, was found to enhance balance performance in healthy elderly persons. At the same time, consequences of low-intensity stimulation on another division of the somatosensory system, which is responsible for sensation of muscle and tendon length and force, are not well understood yet. It is known that vibration of bellies or tendons of ankle muscles, which are important for maintenance of balance during biped standing in humans, elicit sway of the body. The magnitude of sway depends on the frequency of vibration. In healthy persons, the maximal postural effect is produced by 80-100 Hz vibrations; it diminishes with a decrease in frequency, and is not visible with vibrations with frequencies below 30-40 Hz.

According to some embodiments of the present disclosure, to compensate for the above-described decline, stochastic resonance can be induced in the proprioceptive loop with a substantially or completely continuous near-threshold stimulation of muscle proprioceptors. The near-threshold stimulation of proprioceptors may comprise relatively low-frequency vibrations exerted on some portions of the body of the user (e.g., by a device). For example, the near-threshold stimulation can be deployed as low-frequency vibration applied to a portion of a user's leg, such as the lower leg or, more specifically, areas of the shin, which produces stimulation of receptors of the gastrocnemius or "calf" muscle. Alternatively or additionally, the near-threshold stimulation can be deployed as low-frequency vibration applied to a portion of a user's lower back. By way of example, the low frequency vibration can cause repetitive stretching of the adjacent muscle, which may be sufficient enough movement to be detected by the proprioceptors, which then send corresponding signals to the motor neurons.

These signals can elevate an excitability of the motor neurons and increase the probability of generating action potentials, which trigger muscle contractions, changing joint position. In other words, the low frequency vibration may increase the responsiveness of motor neurons to proprioceptive stimuli produced by the natural sway of the body and, thus, facilitate compensatory movements of the body necessary for the maintenance of balance.

Accordingly, the applied low-frequency stimulation can produce resonance-type responses in the proprioceptive loop, which can facilitate motor responses to perturbations in posture. Put another way, embodiments described herein can provide users with low frequency stimulation of proprioceptors, which can then lead to improved responses in the aforementioned response loop. These improved responses can help to achieve needed changes in posture, thereby reducing a likelihood of experiencing an unintentional loss of balance and/or suffering an unintentional fall.

As used herein, the term "threshold stimulation" may be considered as the minimum frequency of vibratory stimulation at which the vibration is consciously perceived by the user. As such, "near-threshold stimulation" may be considered as the stimulation that is substantially close to (e.g., above or below) the threshold stimulation and therefore may include a window or range comprising subthreshold, threshold, and/or above-threshold stimulation frequencies. In some embodiments, the near-threshold stimulation may comprise relatively low-frequency vibrations, such as less than about 40 Hz. In further embodiments, the near-threshold stimulation may comprise relatively low-frequency vibrations, such as between about 20 Hz and about 40 Hz. Notably, an exact threshold stimulation may be different for each user depending on the user's age and/or other characteristics. For example, for some users, threshold may be about 30 Hz, while 40 Hz may be just above threshold. However, as further described below, other frequencies may be contemplated within the scope of this disclosure.

Moreover, it is believed that vibratory stimulation of a muscle with a relatively low frequency (e.g., approximately 40 Hz or a lower frequency) can stimulate proprioceptors, but may not result in any significant motor responses. Put another way, stimulation of proprioceptors at a relatively low frequency (e.g., approximately 40 Hz or below) can induce improved responses to perturbations in posture, but may not induce any significant motor responses, such as muscle contractions.

Accordingly, by applying the device and methods described herein, a user may experience improved balance and reduced risk of loss of balance and/or reduced risk of unintentional falls, which can be attributable to enhancement of proprioceptor sensitivity and potentiation of monosynaptic responses of motor neurons by noise-signals elicited by low-amplitude vibratory stimulation (e.g., stretches) of a parent muscle.

Referring now to FIG. 1, a device 10 is provided for delivering proprioceptive stimulation to a user, in accordance with some embodiments, to reduce the risk of and/or prevent unintentional losses of balance. The device 10 can be employed by any user (e.g., regardless of age, gender, sex, etc.). Furthermore, the device 10 can be employed by a user that may, for example, require or otherwise need and/or wish to use the device 10 to reduce the risk of loss of balance and/or reduce the risk of unintentional falls. Put another way, embodiments of the device 10 may provide additional improvement for users that experience a reduction in the ability to maintain balance and perturbations of posture (e.g., compared to others that generally do not experience such losses or perturbations).

As illustrated in FIG. 1, the device 10 can be configured to engage and/or be worn (i.e., donned) by the user and can include one or more elements that, together, can provide the aforementioned benefits. For example, in some embodiments, the device 10 can comprise a first support member 12, a second support member 14, a sensor 16, a stimulator 18, and a power supply 20.

In some embodiments, the first and second support members 12, 14 can be configured to be coupled to or worn by the user. As such, when a user wishes to employ the device 10, the user can employ the first and second members 12, 14 to don the device 10. For example, in some embodiments, the first support member 12 and/or the second support member 14 can each comprise a generally cuff-like structure configured to wrap around a portion of the user's body, and comprise configurations such as, but not limited to, a sleeve, a wrap, a strap, a band, or another suitable structure. Furthermore, in some embodiments, the first support member 12 and/or the second support member 14 can each comprise a generally continuous and flexible structure that can expand and contract upon the user donning and doffing the device 10 (such as a flexible cuff-like structure). Additionally or alternatively, the members 12, 14 can comprise a cuff-like portion and a separate flexible portion capable of expanding and contracting (such as, but not limited to, a fabric sleeve and an attached elastic band).

Additionally, in embodiments where the first support member 12 and/or the second support member 14 do not form a continuous loop, the member 12, 14 can include a fastening structure, such as Velcro®, one or more snaps, one or more buttons, or other suitable fasteners configured to be engaged when the user dons the member 12, 14 in order support the member 12, 14 in a position relative to the user. Alternatively, or in addition, the member 12, 14 can comprise a structure similar to a belt such that the member 12, 14 can be cinched around a portion of the user. Accordingly, the member 12, 14 can be wrapped around a portion of the user and fastened to itself via one of the fastening methods described above.

It should be noted that, while the first and second support members 12, 14 are collectively described above, they need not include the same properties or fastening structures and, in some embodiments, may comprise different structures than each other, or different structures not specifically described herein.

With respect to the first support member 12, in some embodiments, the first support member 12 can be configured to be worn by the user in a location so that the device 10 can provide proprioceptive stimulation to the user. In other words, the first support member 12 can be generally configured to engage one or more portions of the user's body to provide stimulation of proprioceptors of the one or more portions. For example, in some embodiments, the first support member 12 can be configured to be worn by the user on a lower portion of the user's body, such as adjacent to the user's waist and/or lower back (e.g., generally similar to a belt). In another example, the first support member 12 can be configured to be worn on or around a portion of the user's leg, such as a lower portion or an upper portion of the leg (e.g., as defined by a knee of the user, with the upper portion being above the knee and more proximate to the waist of the user and the lower portion being below the knee and more distal to the waist of the user). In a specific example, the first support member 12 can be configured to be worn on or around a portion of the user's lower leg and, more specifically, can be configured to engage the calf/shin area of the user.

With respect to the second support member 14, in some embodiments, the second support member 14 can be configured to be worn by the user to engage one or more portions of the user's body that change orientation based on the user's activity, as further described below. For example, the second support member 14 can be configured to be worn adjacent to and/or engage an upper or proximal portion of the user's leg, such as the user's thigh (e.g., generally similar to a garter belt).

FIGS. 2A and 2B illustrate example locations of the first support member 12 and the second support member 14 donned by a user. As shown in FIGS. 2A and 2B, the first support member 12 is a cuff- or wrap-like structure configured to be worn adjacent to a region of the lower leg immediately distal to the knee (e.g., adjacent to the shin of the user). More specifically, the first support member 12 is configured to be worn to place at least portions of the device 10 immediately adjacent to the gastrocnemius (i.e., calf muscle) of the user. As further shown in FIGS. 2A and 2B, the second support member 14 is a cuff- or wrap-like structure configured to be worn adjacent to a region of the upper leg proximal to the knee (e.g., adjacent to the mid or lower thigh of the user). Additionally, in some embodiments, as shown in FIGS. 2A and 2B, the device 10 can include two first support members 12 and two second support members 14, where a first support member 12 and a second support member 14 can be worn on each leg of the user.

As noted above, in some embodiments, the device 10 can include a sensor 16. Generally, the sensor 16 can be configured to sense the user's orientation, that is, whether the user is standing (or engaging in movement, such as walking, running, jogging, etc.) or sitting (or lying down). For example, the sensor 16 can be coupled to, supported by, or disposed within the second support member 14, such as within a loop or pocket (not shown) defined by the second support member 14 and sized to receive the sensor 16. Moreover, in some embodiments, the second support member 14 can support a plurality of sensors 16 (not shown). Furthermore, in some embodiments, the sensor(s) 16 can be removable from the second support member 14.

As described above, in some embodiments, the second support member 14 can be configured to be donned on a user's thigh. As such, the sensor 16 can be configured to be positioned at the front, side, or rear of the user's thigh. Notably, when the user stands or walks, the user's thigh is in a substantially vertical position and, when the user sits or lies down, the user's thigh is in a substantially horizontal position. As a result, the sensor 16 can be configured to detect or sense this change between vertical and horizontal orientations.

Accordingly, in some embodiments, the sensor 16 can be configured as a gravitational sensor or accelerometer capable of emitting different signals based on the user's orientation. For example, when the sensor 16 is oriented one way (e.g., when the user is standing and the thigh is substantially vertical), the sensor 16 can emit a first signal (such as an activation signal), and when the sensor 16 is oriented another way (e.g., when the user is sitting and the thigh is substantially horizontal), the sensor 16 can emit a second signal (such as a deactivation signal, which may be, in some applications, a zero or open signal). In one specific example, the sensor 16 can be a gravitational sensor that initiates a connection (e.g., thereby closing a circuit) when in one orientation and opens the connection (e.g., thereby opening the circuit) when in another orientation. Thus, in this example, the sensor 16 can provide a high signal (e.g., the activation signal) via the closed circuit when in one orientation and no signal (e.g., the deactivation signal) via the open circuit when in another orientation.

It should be noted that, while the sensor 16 is described herein as emitting first and second signals, it is within the scope of this disclosure to include sensors 16 capable of emitting more than two signals. Furthermore, in other embodiments, the sensor 16 can be configured and arranged as another structure or device configured to provide activation and/or deactivation signals. For example, the sensor 16 may comprise a chip with or without an integrated circuit and/or any other structure that can be used to provide activation and deactivation instructions.

Generally, the sensor 16 can be arranged relative to the user so that the device 10 can be at least partially controlled by the sensor 16 based on the user's orientation. More specifically, the sensor 16 can be used to provide control over activities of the device 10, that is, to provide control of proprioceptive stimulation, depending on the user's orientation. As further described below, the sensor 16 can provide such control by selectively activating and/or deactivating the stimulator 18.

More specifically, as noted above, the device 10 can include at least one stimulator 18. The stimulator 18 can be at least partially supported by, disposed within, and/or coupled to the first support member 12. For example, in some embodiments, the stimulator 18 can be disposed within a recess or pocket substantially defined by the first support member 12 (and sized to receive the stimulator 18). Moreover, in some embodiments, the stimulator 18 can be disposed within the recess or pocket of the first support member 12 so that the stimulator is substantially or completely retained in place during operation of the device 10. As such, in one embodiment, the stimulator 18 can be configured to be positioned within the first support member 12 so that, when donned by the user, the stimulator 16 is positioned above the belli of the gastrocnemius muscle. Additionally, in some embodiments, the first support member 12 can support and/or be coupled to a plurality of stimulators 18. Furthermore, in some embodiments, the stimulator(s) 18 can be removable from the first support member 12.

Generally, the stimulator 18 can be any type of device capable of providing vibratory stimulation to proprioceptors of the user at a relatively low frequency. In some aspects, the frequency is less than about 100 Hz, less than about 90 Hz, less than about 80 Hz, less than about 70 Hz, less than about 60 Hz, less than about 50 Hz, less than about 40 Hz, less than about 30 Hz, less than about 20 Hz, or less than about 10 Hz. In some embodiments, the frequency is about 40 Hz, about 30 Hz, about 20 Hz, about 10 Hz, or any frequency in between about 100 Hz and about 10 Hz, between about 40 Hz and about 10 Hz, or between about 40 Hz and about 20 Hz. In some embodiments, the frequency may be fixed; however, in other embodiments, the frequency may be adjustable, as further described below.

In some embodiments, the stimulator 18 can be configured as an eccentric motor. In further embodiments, the eccentric motor can be configured as an eccentric rotating mass vibration motor. In one specific example, the stimulator 18 can be a direct drive motor with an attached eccentric load, for example, enclosed in a barrel and capable of sufficient amplitude of movement during vibration (in one application, a 1-millimeter amplitude is sufficient; however, other amplitudes may be sufficient in other applications). In other embodiments, the stimulator 18 can be a linear motor. In such embodiments, the linear motors may be employed or mounted flush against the portion of the user's body (e.g., may be held in place against the portion of the user's body via the pocket or loop of the first support member 12, as described above, may be held in place directly against a portion of the user's body via a support member 12 in the form of an elastic band or wrap, may be held in place directly against a portion of user's body via a support member 12 in the form of tape secured to the user's body, or may be positioned in other suitable ways).

To the extent that the first support member 12 and the stimulator 18 are disposed substantially adjacent to the lower leg, the vibrational movement of the stimulator 18 can provide proprioceptive stimulation to a portion of the lower leg, such as the gastrocnemius. In other embodiments, the stimulator 18 or one or more of the plurality of stimulators 18 can comprise any other structure and configuration that is capable of providing proprioceptive stimulation to muscle spindles of the user to aid the user in maintaining and/or improving balance and/or reducing the risk of unintentional falls. As described above, in some embodiments, the stimulator 18 can provide proprioceptive stimulation without inducing muscle contractions or otherwise activating muscles. For example, the proprioceptive stimulation can be provided with a relatively low-level frequency (e.g., approximately 40 Hz or under) to induce proprioceptive stimulation, but not trigger muscle contractions. By failing to induce muscle contractions, the device 10 enhances balance through proprioceptive stimulation, but will not cause the user the physical and psychological discomfort of ongoing muscle contractions.

In some embodiments, the stimulator 18 can be activated and deactivated by a power button 22 (optionally shown in FIG. 1) positioned at any location on the device 10, such as on the first support member 12. Additionally, in some embodiments, the stimulator 18 can be activated and deactivated by the sensor 16. More specifically, the sensor 16 can be configured to provide operative communications (e.g., activation and deactivation signals) to the stimulator 18. For example, the stimulator 18 can receive the activation signal from the sensor 16 to initiate movement (e.g., vibrational movement) of the stimulator 18. The stimulator 18 and the sensor 16 can communicate via a wired connection 24, as shown in FIGS. 1-2B, or via a wireless communication (such as, but not limited to, a Bluetooth® connection or any other suitable wireless communication technologies).

In some embodiments, the stimulator 18 can be activated and deactivated by the sensor 16 based on the orientation of the user. More specifically, proprioceptive stimulation and balance control may only be necessary while the user is standing. As a result, the sensor 16 can be employed such that a change of orientation (e.g., moving from sitting to standing or vice versa) can provide a change in the activation state of the stimulator 18. For example, the sensor 16 and the second support member 14 can be donned by the user generally adjacent to the mid-thigh, as described above, so that when the user stands or the user's thigh is disposed in a substantially vertical position, the sensor 16 provides an activation signal to the at least one stimulator 18 to provide stimulation to proprioceptors. Moreover, when the user sits or the user's thigh is disposed in a substantially horizontal position, the sensor 16 provides a deactivation signal to the stimulator 18 to substantially or completely cease providing stimulation to proprioceptors.

In some embodiments, some or all of the stimulators 18 may be configured to operate in unison upon receiving an activation or deactivation signal from the sensor 16. In other aspects, some or all of the stimulators 18 may operate on different activation and deactivation signals from the sensor 16 (or sensors 16) such that not all of the plurality of stimulators 18 operate at the same time and/or provide the same level of proprioceptive stimulation.

In some embodiments, in addition to or alternative to the power button, the device 10 can include one or more switches, knobs, or dials 26 (optionally shown in FIG. 1) configured to control the vibration frequency of the stimulator 18 based on user input. For example, in one embodiment, the device 10 can include one or more switches 26 configured to adjust the vibration frequency of the stimulator 18 to one or more set frequencies, such as about 20 Hz, about 30 Hz, about 40 Hz, and/or other frequencies. In some embodiments, the adjustments may be at set intervals, such as 1 Hz, 5 Hz, 10 Hz, or other intervals. For example, in some embodiments, the one or more switches 26 can be used to adjust the vibration frequency based on the user's personal sensitivity to the vibrations (e.g., based on the user's specific threshold level). Upon such adjustments, the stimulator 18 can vibrate at that frequency when activated. In some embodiments, the device 10 can include a controller (not shown) in communication with the switch 26 and the stimulator 18 and can be configured to interpret user input via the switch 26 to control the frequency of the stimulator 18. However, in other embodiments, no controller is needed and the switch 26 may be in operative communication with the stimulator 18 to control the output frequency of the stimulator 18. Additionally, in some embodiments, the switch 26 can be positioned at any location on the device 10, such as on the first support member 12, as shown in FIG. 1.

Furthermore, as noted above, the device 10 can include a power supply 20. The power supply 20 can be operatively coupled to and used to power, for example, the stimulator 18 and/or the sensor 16. For example, as shown in FIG. 1, the power supply 20 can be operatively coupled to the stimulator 18 via a connector 28. Additionally, in some embodiments, the power supply 20 can be in communication with the power button 22, the switch 26, and/or the controller. In some embodiments, the power supply 20 can be configured as a battery (e.g., a primary cell or non-rechargeable battery or a secondary cell or rechargeable battery), such as an alkaline battery, a lithium ion battery, a nickel-cadmium battery, or another suitable power source.

In some embodiments, the power supply 20 can also be disposed within, coupled to, and/or supported by the first support member 12, as shown in FIG. 1. For example, in some embodiments, the power supply 20 can be disposed substantially adjacent to the stimulator 18 within the first support member 12, as shown in FIGS. 1-2B. In other embodiments, the power supply 20 can be supported by the second support member 14 and/or may be otherwise worn by the user.

In some aspects, with respect to a circuit arrangement, the power supply 20 can be disposed between the stimulator 18 and the sensor 16 (and/or between the stimulator 18 and the switch 26). As such, the sensor 16 can be in communication with power supply 20 (e.g., via wired communication 24, as shown in FIG. 1, or wireless communication) and/or the stimulator 18. In some embodiments, the sensor 16 may be in direct operative communication with the power supply 20 and indirect operative communication with the stimulator 18. For example, the sensor 16 can provide an activation signal to the power supply 20, causing the power supply 20 to provide current to the stimulator 18 to initiate generation of proprioceptive stimulation (that is, initiate the stimulator 18 to vibrate). Conversely, the sensor 16 can provide a deactivation signal to the power supply 20, causing the power supply 20 to decrease or eliminate the current flowing to the stimulator 18 to reduce or eliminate generation of proprioceptive stimulation (that is, to stop vibration of the stimulator 18). For example, the sensor 16 can act to close a circuit between the power supply 20 and the stimulator 18 when in one orientation, and can open the circuit when in another orientation.

In light of the above, following paragraph includes a general and exemplary illustration of how a user may employ some embodiments of the device 10. The following example is intended for illustrative purposes and use of the device 10 in other manners may be contemplated within the scope of this disclosure.

For example, the device 10 may be employed by initially donning the device 10 (e.g., over or under clothing of the user). The second support member 14 can be worn on a lower or mid-thigh of the user so that the sensor 16 is able to distinguish when the user's thigh is in a substantially horizontal position (e.g., seated or lying down) or in a substantially vertical position (e.g., standing or walking). In addition, the first support member 12 can be worn and positioned so that the stimulator 18 is substantially adjacent to the gastrocnemius or back of the user. After being donned, the sensor 16 can be used to activate the device 10 (e.g., by activating the power supply 20 to provide current to the stimulator 18) when the user is standing. As such, the stimulator 18 is activated and provides proprioceptive stimulation to the gastrocnemius (or lower back) of the user to provide the aforementioned benefits. Upon the user returning to a seated position, the sensor 16 provides a deactivation signal to the power supply 20, which then ceases providing current to the stimulator 18, thereby ending proprioceptive stimulation. As such, the device 10 is able to provide proprioceptive stimulation only when the user is at risk for losing balancing and experiencing an unintentional fall (i.e., when standing). Illustratively, FIG. 2A depicts the user seated such that the device 10 is in a deactivated state and FIG. 2B depicts the user standing such that the device 10 is in an activated state.

Figure 3:
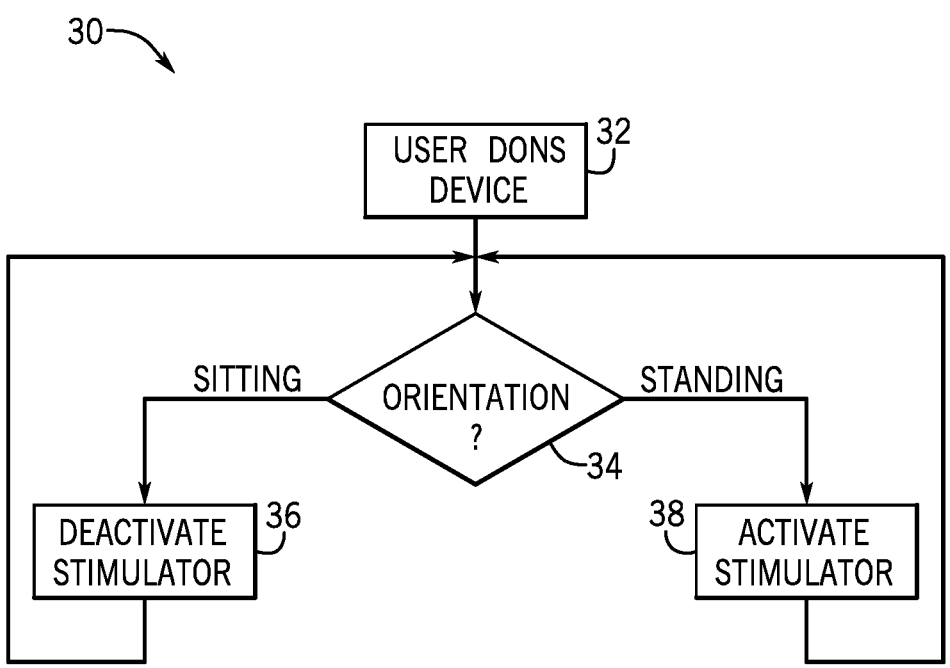
FIG. 3 is a flow chart illustrating a method, according to some embodiments, of reducing a risk of unintentional falls and/or enhancing balance.

In light of the above example, FIG. 3 illustrates a method 30, according to some embodiments, of reducing a risk of unintentional falls and/or maintaining balance. As shown in FIG. 3, the method 30 includes a user donning the device at step 32. At step 34, an orientation determination is made, for example, based on the sensor 16. If, at step 34, the sensor 16 senses that the user is sitting, the stimulator 18 is deactivated at step 36. If, at step 34, the sensor 16 senses that the user is standing (or walking), the stimulator 18 is activated at step 38. In some applications, steps 32-38 may be repeated until the user takes off the device 10 and/or until the user turns off the device 10, for example, via the power button 22.

The following paragraphs provide a discussion of methodologies and results connected with analyses of some embodiments of the aforementioned device 10. The following paragraphs are not intended to limit the instant disclosure in any manner.

In particular, according to a first study, postural stability was examined in 10 young subjects (YS, 23±2 years) and 19 old subjects (OS, 78±9 years), with 10 OS having a history of falls. The device 10 was positioned as illustrated in FIGS. 2A and 2B. Proprioceptive stimulation was produced by 30 Hz frequency vibration using the stimulator 18 (i.e., an eccentric motor) enclosed in the first support member 12 (e.g., a sleeve) and positioned adjacent to the gastrocnemius muscle on both shins. Standing without vibration was tested first. Following one minute for adaptation to the device 10, standing with shin vibration was tested. Each test lasted thirty seconds. During testing, subjects kept their eyes closed to exclude visual control of posture and limit postural control to proprioceptive and vestibular systems.

Standing balance was evaluated using an FDA-approved device, BalanSENS (BioSensics, Watertown, Mass.). The subjects wore motion sensors 40 (e.g., triaxial gyroscope sensors) on the right shin and on the waist (as shown in FIGS. 2A and 2B). Using these sensors 40, anterio-posterior and medio-lateral angular deviations in the subject's ankle and hip joints were measured. Position of the center of mass (COM) in the horizontal plane and the range of movement thereof during a test were estimated using the acquired ankle and hip angular deviations and a biomechanical model of the human body. Fall risk was determined using a STEADI falls assessment score. To assess postural stability (i.e., maintenance of balance) with and without proprioceptive vibration, a range of COM during vertical position (i.e., standing) was evaluated. Generally, a lower COM range indicates better balance.

During standing without shin vibration, in the YS group, the range of COM position varied among subjects from 0.19 to 1.6 $cm^2$, and on average was 0.65±0.33 $cm^2$, while in the OS group, the range of COM position varied among subjects in a wider range from 0.22 to 2.22 $cm^2$, and on average was 0.81±0.54 $cm^2$. When the device 10 was activated and providing proprioceptive stimulation, the range of COM position increased in 8 (80%), and decreased in 2 (20%) of the YS group. Thus, with activation of the device 10, in the YS group, variability of range of COM position expanded from 0.2 to 4.08 $cm^2$ and on average increased to 1.32±1.22 $cm^2$ (p=0.067, two-tailed t-test). However, the effect of proprioceptive stimulation in the OS group was different: the range of COM position and movement increased in a smaller part of the group (7/19, 37%), but decreased in a larger part of the group (12/19, 63%).

These results generally illustrate that embodiments of the device 10 can provide benefits to individuals that need assistance in maintaining balance and preventing unintentional falls. More specifically, the device 10 may improve balance and reduce risk of unintentional falls in those in need, such as older subjects, but may not be effective for those who are at lesser risk, such as younger subjects.

Figure 4A:
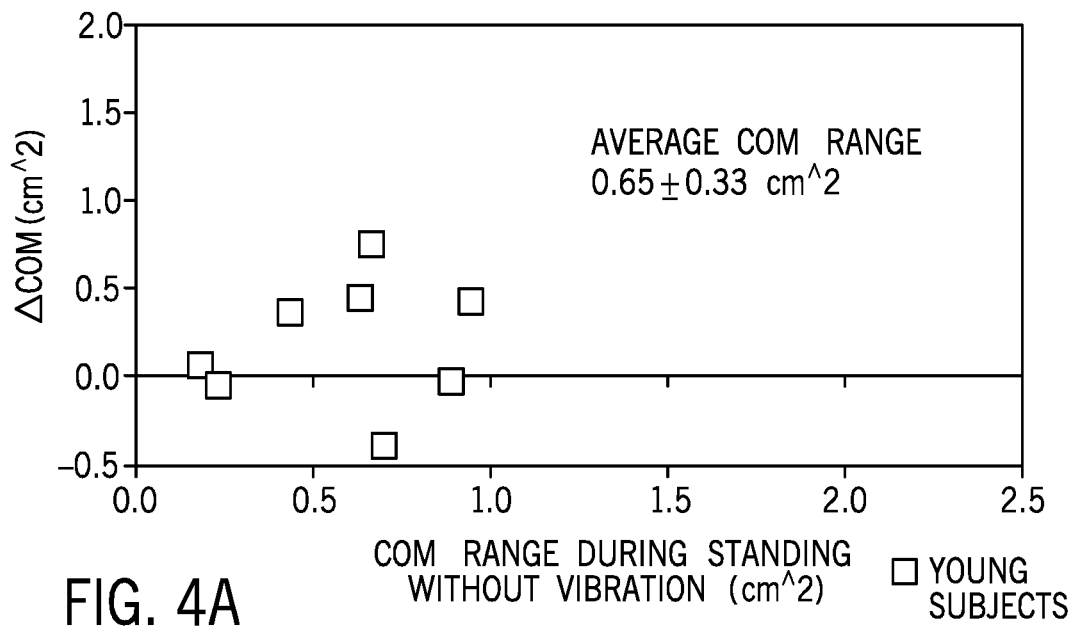
FIGS. 4A and 4B are graphs illustrating results of a study conducted to assess the efficacy of embodiments of the device to provide proprioceptive stimulation to enhance balance and reduce the risk of unintentional falls in young subjects and elderly subjects, where
Figure 4B:
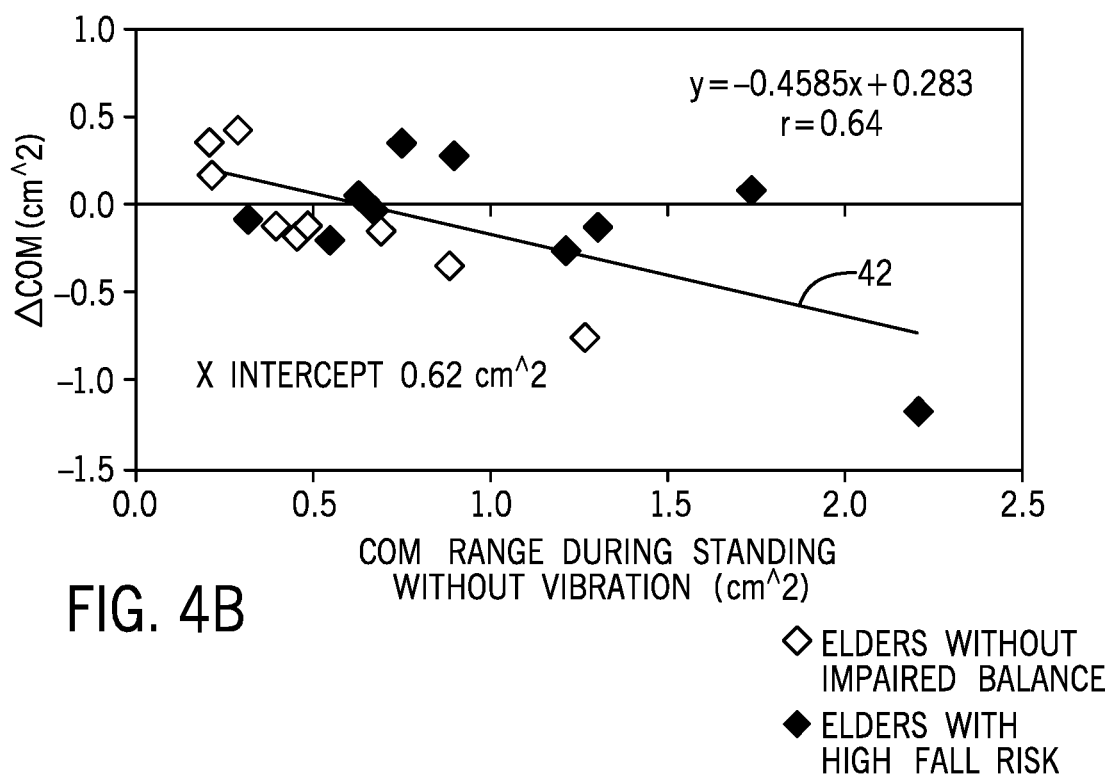

To further illustrate this principle and to analyze postural responses of the groups to proprioceptive stimulation, the relationship between a change in COM range (ΔCOM) during stimulation and COM range during standing without vibration was examined (as generally illustrated in FIG. 4A, with respect to the YS group, and 4B, with respect to the OS group). During proprioceptive stimulation, COM range tended to increase in subjects with an initial small COM range (e.g., those with better balance), but tended to decrease in subjects with an initial large COM range during standing without proprioceptive stimulation (e.g., those with worse balance). For the OS group, as shown in FIG. 4B, the relationship between ΔCOM and COM range during standing without vibration was approximated with a linear regression line 42 having a negative slope (ΔCOM=−0.46*COM+0.28 (r=0.64)). The regression line 42 intercepted the x-axis at COM range of 0.62 $cm^2$.

Noteworthy, the intercept value was almost identical to the average COM range during standing without proprioceptive stimulation in YS. Furthermore, this interception divided the OS group in two subgroups: stable OS, with low COM range during standing without proprioceptive stimulation, and unstable OS, with large COM range during standing without proprioceptive stimulation. The subgroup of stable OS consisted of eight subjects. In six (75%) of the stable OS group, ΔCOM was positive, and in two (25%) ΔCOM was negative during proprioceptive stimulation; also, six subjects of this subgroup did not have postural disturbances in the past, while two subjects experienced falls. The subgroup of unstable OS consisted of eleven subjects. In four (36%), ΔCOM was positive, and in seven (64%), ΔCOM was negative during proprioceptive stimulation; also, three subjects (27%) of this subgroup did not have postural disturbances in the past, but eight subjects (72%) experienced falls. A binomial distribution test showed that a probability of a member of unstable OS subgroup to experience a fall was 0.92. Proprioceptive stimulation using embodiments of the device 10 could decrease COM range during standing in the unstable OS subgroup, and shift it toward the COM range of stable subjects. The results of this experimental study indicate that low frequency proprioceptive stimulation may increase postural stability during standing in those at high fall risk, and has the potential to reduce the risk of falls, but may not significantly benefit young subjects and elders with unimpaired balance.

Figure 5A:
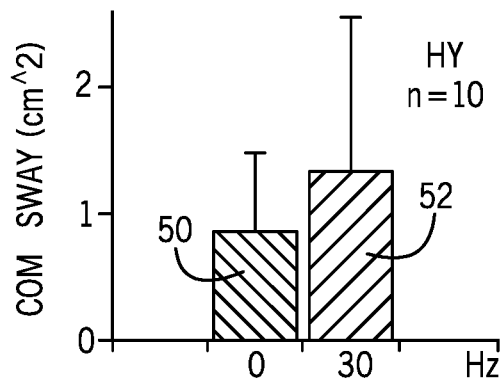
FIGS. 5A-5F are graphs illustrating results of a study conducted to assess the efficacy of embodiments of the device to provide proprioceptive stimulation to enhance balance and reduce the risk of unintentional falls in healthy young subjects (HY), healthy elderly subjects (HE), and elderly subjects with fall risk (FR), where
Figure 5B:
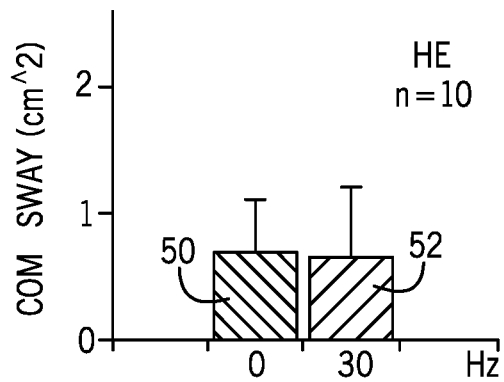
Figure 5C:
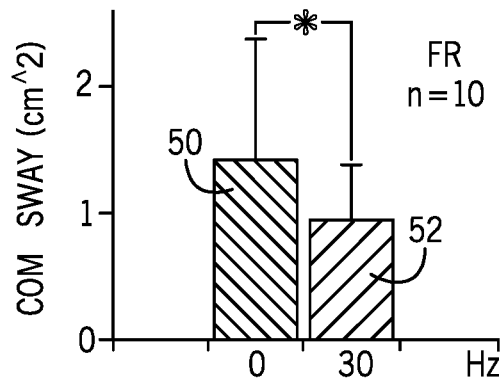
Figure 5D:
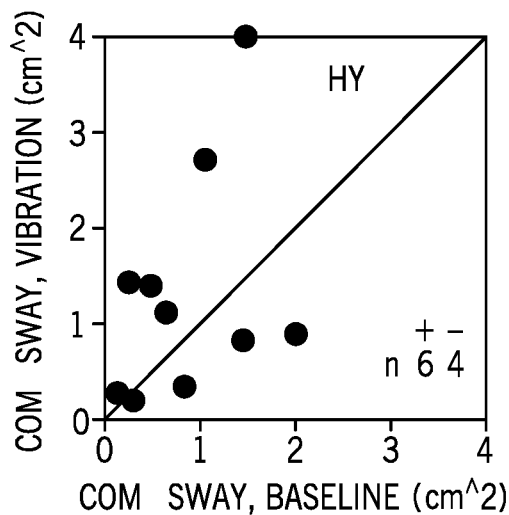
Figure 5E:
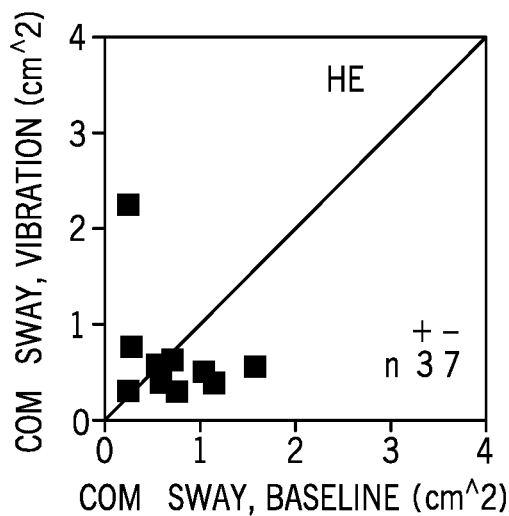
Figure 5F:
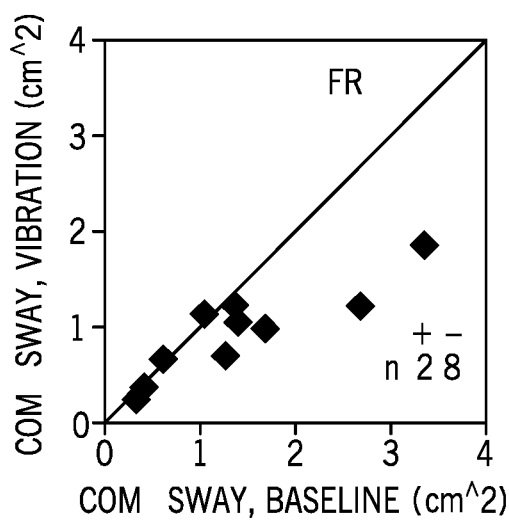

FIGS. 5A-5F illustrate differences in COM sway with and without 30 Hz proprioceptive vibration. More specifically, FIGS. 5A, 5B, and 5C are bar graphs illustrating average COM sway without vibration 50 and with 30 Hz proprioceptive vibration 52 for the HY group, the HE group, and the FR group, respectively. FIGS. 5D, 5E, and 5F are graphs illustrating COM sway during proprioceptive vibration as a function of baseline (i.e., no vibration) COM sway for the HY group, the HE group, and the FR group, respectively. Additionally, Table 1 below illustrates differences in assessed parameters (COM anterio-posterior (AP), COM medio-lateral (ML), and COM sway) before and during vibration using repeated measures MANOVA. Differences in frequencies of parameter increases (+) and decreases (−) that occurred during vibration were assessed using $\chi^2$ test. Within Table 1, statistically significant differences between the balance parameter in two conditions (p<0.05) are indicated by a single star (*), while differences between the balance parameter that are just above statistical significance (0.1<p<0.05) are indicated by two stars (**).

TABLE 1

COM displacements and sway in persons standing with eyes closed before and during 30 Hz shin vibration.

|  | Healthy Young | Healthy Elderly | Fall Risk Elderly | Group difference |
|---|---|---|---|---|
| COM AP (cm) | | | | |
| Before vibration | 1.21 ± 1.08 | 1.12 ± 0.45 | 1.68 ± 0.64 | F(2, 9) = 3.43, |
| During vibration | 1.55 ± 0.89 | 1.25 ± 0.63 | 1.39 ± 0.47 | p = 0.0472* |
|  | F(1, 9) = 1.63, | F(1, 9) = 0.25, | F(1, 9) = 19.43, | |
|  | p = 0.2338 | p = 0.6268 | p = 0.0017* | |
|  | (+) 7 (−) 3 | (+) 5 (−) 5 | (+) 0 (−) 10 | |
|  | p = 0.2059 | p = 1.0 | p = 0.0016* | |
| COM ML (cm) | | | | |
| Before vibration | 1.21 ± 1.08 | 1.12 ± 0.45 | 1.68 ± 0.64 | F(2, 9) = 3.24, |
| During vibration | 0.86 ± 0.19 | 0.73 ± 0.21 | 0.86 ± 0.24 | p = 0.0550** |
|  | F(1, 9) = 2.34, | F(1, 9) = 0.07, | F(1, 9) = 5.31, | |
|  | p = 0.1607 | p = 0.7941 | p = 0.0467* | |
|  | (+) 8 (−) 2 | (+) 5 (−) 5 | (+) 2 (−) 8 | |
|  | p = 0.0568** | p = 1.0 | p = 0.0568** | |
| COM sway (cm^2) | | | | |
| Before vibration | 0.86 ± 0.62 | 0.69 ± 0.43 | 1.40 ± 0.96 | F(2, 9) = 2.74, |
| During vibration | 1.32 ± 1.20 | 0.66 ± 0.57 | 0.94 ± 0.47 | p = 0.0822** |
|  | F(1, 9) = 1.63, | F(1, 9) = 0.02, | F(1, 9) = 6.47, | |
|  | p = 0.2340 | p = 0.8861 | p = 0.0316* | |
|  | (+) 6 (−) 4 | (+) 3 (−) 7 | (+) 2 (−) 8 | |
|  | p = 0.5271 | p = 0.2059 | p = 0.0568** | |

According to another study, postural stability was examined in thirty subjects divided into three groups: healthy young subjects (HY, 10 subjects, five males and five females (23.3±2.3 years)), healthy elderly persons (HE, 10 subjects, three males and seven females (72.9±2.8 years)), and elderly persons at high risk of fall (FR, 10 subjects with 3±4.6 falls within one year, three males and seven females (83.6±9.6 years)).

The same device 10 and general methods described above were used in this study. To assess postural stability of the subjects (i.e., maintenance of balance) with and without proprioceptive vibration, COM displacements during vertical position (i.e., standing) with eyes closed were evaluated. Balance parameters in the three groups of subjects were compared using ANOVA and post-hoc Tukey HSD test.

As shown in Table 1, during standing without shin vibration, balance parameters were similar in the two groups of healthy participants (HY and HE). At variance, participants of the FR group had a substantially higher range of COM displacements during quiet standing. In the FR group, COM anterio-posterior (AP) displacements were significantly larger, and COM medio-lateral (ML) displacements, as well as COM sway were almost significantly larger than these parameters in both HY and HE groups.

When the device 10 was active and vibrated shins, thus providing proprioceptive stimulation, only a few changes were seen in the balance parameters in the HY and HE groups (as shown in Table 1 and FIGS. 5A, 5B, 5D, and 5E). Only the HY group experienced a noticeable increase in COM ML displacements. In contrast, statistically significant changes in balance parameters occurred during shin vibration in the FR group, and COM AP and ML displacements as well as COM sway decreased significantly (as shown in Table 1 and FIG. 5C). In particular, COM AP displacements decreased in 100% of participants of the FR group, while both COM ML displacements and COM sway decreased in 80% of participants of the FR group (as shown in Table 1 and FIG. 5F).

The results of this experimental study indicate that low frequency proprioceptive stimulation can increase postural stability during standing for elders at high fall risk. Young subjects and elders with unimpaired balance are not significantly affected by such shin vibrations. The results illustrate that embodiments of the device 10 have a potential to provide benefits to individuals that need assistance in maintaining balance while reducing the risk of unintentional falls while standing and walking. By way of example, someone with imperfect vision may wear glasses to correct their vision. However, those glasses would have the opposite effect on someone with perfect or good vision and, instead, blur their vision. Similarly, here, the device 10 may improve balance in those who are in need, but may have no effect or a worsening effect for those who generally have good balance. In other words, such stimulation may disturb the function of a well-balanced neuromuscular system, but improve the function of a declining neuromuscular system.

In light of the above, the embodiments of the disclosure provide a device and methods to provide proprioceptive stimulation to relevant muscle groups that may play a role in maintaining balance. As a result, the device and methods can help improve postural performance and reduce a risk of loss of balance or unexpected falls for those in need. Moreover, the device comprises minimal parts and uses anatomy of the user's body to control operation. This simple operation (e.g., providing a sensor that turns vibration on and off based on user orientation) can increase reliability compared to more complex devices and can provide the above benefits at a relatively low cost to the user, which is desirable because of rising medical expenses for the elderly. Additionally, by providing vibrational stimulation, the device can be considered non-invasive and, by failing to induce muscle contractions, the device generally will not cause the user the physical and psychological discomfort of ongoing muscle contractions.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto. Also, throughout the disclosure, the term "about" means a range of plus or minus 20% with respect to the specified value, more preferably plus or minus 10%, even more preferably plus or minus 5%, most preferably plus or minus 2%. In the alternative, as known in the art, the term "about" indicates a deviation, from the specified value, that is equal to half of a minimum increment of a measure available during the process of measurement of such value with a given measurement tool.

All references contained herein are hereby incorporated by reference for any and all purposes of supporting the instant specification, including the following: Ambrose A F, Paul G, Hausdorff J M. Risk factors for falls among older adults: A review of the literature. Maturitas 2013; 75: 51-61; Iliopoulos F, Nierhaus T, Villringer A. Electrical noise modulates perception of electrical pulses in humans: sensation enhancement via stochastic resonance. Journal of Neurophysiology 2014; 111: 1238-48; Gravelle D C, Laughton C A, Dhruv N T, et al. Noise-enhanced balance control in older adults Neuroreport 2002; 13: 1853-6; Priplata A A, Niemi J B, Harry J D, Lipsitz L A, Collins J J. Vibrating insoles and balance control in elderly people. Lancet 2003; 362: 1123-4; Horak F B, Nashner L M. Central programming of postural movements: adaptation to altered support-surface configurations. Journal of Neurophysiology 1986; 55: 1369-81; Cordo P, Inglis J T, Verschueren S, et al. Noise in human muscle spindles Nature 1996; 383: 769-70; Martinez L, Perez T, Mirasso C R, Manjarrez E. Stochastic resonance in the motor system: Effects of noise on the monosynaptic reflex pathway of the cat spinal cord. Journal of Neurophysiology 2007; 97: 4007-16.

What is claimed is:

1. A device for providing proprioceptive stimulation to a user, the device comprising:
   a first support member configured to be worn by the user;
   a second support member configured to be worn by the user;
   a stimulator at least partially supported by the first support member, the stimulator configured to stimulate proprioceptors of the user at a frequency without inducing muscle contraction;
   a sensor at least partially supported by the second support member, the sensor configured to control operation of the stimulator based on an orientation of the user; and
   wherein the stimulator is one of an eccentric motor and a linear motor configured to provide vibrational stimulation.

2. The device of claim 1, wherein the sensor is in wired communication with the stimulator.

3. The device of claim 1, wherein the sensor is in wireless communication with the stimulator.

4. The device of claim 1, wherein the frequency is less than 40 Hz.

5. The device of claim 1, wherein the frequency is one of about 30 Hz, about 20 Hz, and about 10 Hz.

6. The device of claim 1, wherein the first support member is configured to be worn on one of a lower leg and a lower back of the user.

7. The device of claim 1, wherein the first support member is configured to be worn on a lower leg of the user and the stimulator is supported by the first support member to stimulate proprioceptors of a gastrocnemius muscle of the user.

8. The device of claim 1, wherein the first support member includes one of a pocket and a recess sized to receive the stimulator.

9. The device of claim 1, wherein the second support member is configured to be worn on an upper leg of the user.

10. The device of claim 1, wherein the sensor is one of gravity sensor and an accelerometer.

11. The device of claim 1, wherein the sensor is configured to activate the stimulator when the user is in a substantially standing position or walking.

12. The device of claim 11, wherein the sensor is configured to deactivate the stimulator when the user is in a substantially seated position or lying down.

13. The device of claim 1 and further comprising an adjustment switch configured to alter the frequency based on user input.

* * * * *